United States Patent [19]

Menez et al.

[11] Patent Number: 5,164,315
[45] Date of Patent: Nov. 17, 1992

[54] BASIC PROTEIN PHOSPHOLIPASE A2

[75] Inventors: André Menez, St Remy Les Chevreuse; Serge Chwetzoff, Gif sur Yvette, both of France

[73] Assignee: Commissariat a l'Energie Atomique, Paris, France

[21] Appl. No.: 653,133

[22] Filed: Feb. 11, 1991

Related U.S. Application Data

[63] Continuation of Ser. No. 272,405, Nov. 17, 1988, Pat. No. 5,045,462.

[30] Foreign Application Priority Data

Nov. 20, 1987 [FR] France ................................. 87-16096

[51] Int. Cl.$^5$ .............................................. C12N 9/20
[52] U.S. Cl. ...................................................... 435/198
[58] Field of Search .......................................... 435/198

[56] References Cited

PUBLICATIONS

Joubert, Biochimica and Biophysra Acta, 493, pp. 216-227 (1977).

J. B. Harris, Snake Toxins, Ch. 3 pp. 91-129, A. L. Harvey, Ed. 1991 Pergamon Press, Inc.

Primary Examiner—Joan Ellis
Attorney, Agent, or Firm—Oblon, Spivak, McClelland, Maier & Neustadt

[57] ABSTRACT

The present invention relates to a basic protein called phospholipase A2 (PLA2), isolated from the venom of a snake of the family Elapidae, especially of a Naja snake and more particularly *Naja nigricollis* and/or *Naja mossambica pallida*, to the fragments and derivatives of the said protein, to their methods of preparation, to pharmaceutical compositions which can be used to human and/or veterinary medicine, and to diagnostic agents in which the said protein and/or its derivatives and/or its fragments are present.

The said protein comprises 118 amino acids, its molecular weight is of the order of 13,300 Daltons and its isoelectric point is of the order of 8.6.

The derivatives of the said protein are modified at one of the histidines by fixation of an alkyl group of the formula R—CH$_2$—X.

Application to the detection of tumoral cells.

2 Claims, 2 Drawing Sheets

BASIC PROTEIN CALLED PHOSPHOLIPASE A2, ISOLATED FROM THE VENOM OF A SNAKE OF THE FAMILY ELAPIDAE, AND ITS AMINO ACID SEQUENCE, DERIVATIVES AND FRAGMENTS OF THE SAID PROTEIN, THEIR METHOD OF PREPARATION, THERAPEUTIC COMPOSITIONS AND DIAGNOSTIC AGENTS

This is a continuation of application Ser. No. 07/272,405, filed on Nov. 17, 1988.

BACKGROUND OF THE INVENTION

The present invention relates to a basic protein isolated from the venom of a snake of the family Elapidae, especially of a Naja snake and more particularly *Naja mossambica pallida* and/or *Naja nigricollis*, the said protein being called phospholipase A2 (PLA2), to fragments and derivatives of the said protein, to their methods of preparation, to therapeutic compositions which can be used in human and/or veterinary medicine and to diagnostic agents in which the said protein and/or its derivatives and/or its fragments are present.

Numerous antitumoral agents, which are either organic or inorganic substances, exist at the present time. These various agents act on the cell nucleus, in particular the nucleus of tumoral cells. There are several mechanisms of action according to the substance in question: either the said substances interfere with the biosynthesis of the nucleic acids and the proteins, or they interfere with the duplication of the DNA, or they act on the mitotic spindle. A number of authors have demonstrated these different mechanisms of action (R. K. RALPH et al., TIBS, 1983, 212-214; LIPPARD, Science, 1982, 218, 4577, 1075-1082; FAUVAUDON, Biochimie, 1982, 64, 457-475).

However, anticancer substances do not exert their action specifically on cancerous cells. They inhibit the division of healthy cells as well as cancerous cells, so they are toxic to all tissues in which the cells renew themselves rapidly. The various antitumoral substances referred to therefore have a large number of undesirable effects in man.

The magnitude of the undesirable effects has led to the search for new antitumoral agents which have a different mode and site of action and which do not have undesirable effects such as those encountered with the existing antitumoral substances.

It has recently been shown that certain substances secreted by cells of various lines, such as, in particular, B and T lymphocytes as well as macrophages (Ruddle, Immunol. Today, 1987, 8, 5, 129-130), are capable of killing the cells of certain tumoral lines. The genes (cDNA) coding for these substances have been cloned (GRAY et al., Nature, 1984, 312, 721-724; PENNICA et al., Nature, 1984, 312, 724-727). These substances are known as tumor necrosis factors (TNF) and lymphotoxins (LT); it should be noted that the mechanism of action of these substances is not known at the present time.

There is another extremely valuable group of substances, which are substances present in snake venoms; the latter are in fact capable of killing cancerous cells of numerous lines (CHAIM-MATYAS et al., Life Sciences, 1987, 40, 16, 1601-1607); the authors of this publication have shown in particular that snake venoms have a cytotoxic activity towards certain melanomas and chondrosarcomas, both in vitro and in vivo, and especially that the venom of *Naja nigricollis* has a high cytotoxic activity.

This cytotoxic activity seems to be based on a mechanism of membrane lysis of the cells in question which is totally different from the mechanisms of action of the antitumoral substances of the prior art.

The venom of the spitting cobra of East Africa, *Naja nigricollis*, like the venom of the majority of the Elapidae, contains three classes of toxic protein: curarizing toxins, cardiotoxins and phospholipases.

The cardiotoxin, which is the preponderant component of the venom, is responsible inter alia for the cytotoxic action; however, the cytotoxic activity of the total venom is very much greater than that of the cardiotoxin alone. Moreover, the cytotoxic action of the venom is retained in the presence of calcium, which is an inhibitor of the cytotoxic activity of cardiotoxins. One or more cytotoxic factors other than the cardiotoxin are therefore present in the venom of Naja, in particular *Naja nigricollis*.

The phospholipases are classed in different groups according to their lethality. The first group includes acidic or neutral phospholipase A2's, which have a low toxicity; these PLA2's essentially ensure digestion of the phospholipidic tissues. The second group is made up of extremely toxic PLA2's; these are either monomeric basic molecules or molecules containing a basic subunit. These compounds are found in numerous snake venoms and cause rapid paralysis of the prey. They are characterized by an ability to block the release of acetylcholine at the presynaptic nerve endings and by other effects, including substantial myotoxicity in particular. The third group comprises strongly basic, toxic PLA2's; these are found in a number of snake venoms, but their role and their mechanism of action were not well understood until now; the basic PLA2 of *Naja nigricollis* belongs to this category.

GENERAL DESCRIPTION OF THE INVENTION

The object of the present invention was consequently to provide a protein, isolated from the venom of a Naja snake, which has valuable therapeutic properties in man.

A further object of the invention is to provide fragments of the said protein which have an antitumoral activity without being toxic.

A further object of the invention is to provide derivatives of the said protein which are obtained by treating the latter with an appropriate agent and which have an antitumoral activity without being toxic.

A further object of the invention is to provide a method of isolating the said protein.

A further object of the invention is to provide a method of preparing the derivatives and/or fragments of the said protein.

A further object of the invention is to use the said derivatives and/or fragments in pharmaceutical compositions.

A further object of the invention is to use the said derivatives and/or fragments as agents for the selective detection of tumoral cells.

A further object of the invention is to provide a ready-to-use kit for the selective detection of tumoral cells.

The present invention relates to a basic protein of the phospholipase A2 (PLA2) type, isolated from the venoms of snakes, especially of the family Elapidae, which protein comprises 118 amino acids, whose molecular weight is of the order of 13,325 Daltons, whose isoelectric point is of the order of 8.6, which is obtained from the venom of a snake of the family Elapidae, especially of a Naja snake and more precisely *Naja nigricollis* or *Naja mossambica pallida*, or, if appropriate, by synthesis or by cloning and which has both an enzymatic activity and a cytotoxic activity.

The molecular weight was determined by gel filtration (PAGE-SDS) with reference to the alphaneurotoxin of *Naja nigricollis* (MW: 6800), to cytochrome C (MW: 12,500), to the inhibitor of soya germ trypsin (MW: 21,500) and to bovine serum albumin (MW: 68,000).

In an advantageous embodiment of the said protein, it has formula I below:

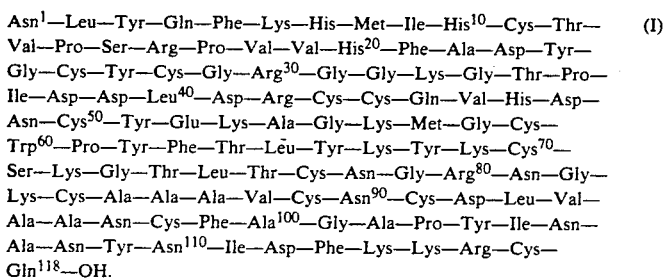

The inventors have demonstrated that the lethal toxic action of the said protein is due to the conjugation of two actions, namely a cytotoxic action and an enzymatic action.

The invention further relates to the fragments and/or derivatives of the said protein which have a cytotoxic activity identical or analogous to that of the said protein.

Apart from having a cytotoxic activity analogous to that of phospholipase A2, these derivatives and/or fragments do not have the enzymatic activity of the latter, so they are not toxic, one of the components of the above-mentioned conjugation of actions being absent, but the said derivatives nevertheless having a selective antitumoral activity.

Among the said fragments, the invention encompasses, inter alia:

a peptide consisting of a fragment of PLA2 and having the following amino acid sequence, which corresponds to the amino acids in positions 1 to 8 of the said protein:

Asn$^1$-Leu-Tyr-Gln-Phe-Lys-Asn-Met$^8$-, a peptide consisting of a fragment of PLA2 and having the following amino acid sequence, which corresponds to the amino acids in positions 55-59 of the said PLA2;

Gly$^{55}$-Lys-Met-Gly-Cys$^{59}$-, and a peptide consisting of a fragment of PLA2 and having the following amino acid sequence, which corresponds to the amino acids in positions 44-50 of the said PLA2:

Cys$^{44}$-Gln-Val-His-Asp-Asn-Cys$^{50}$-.

The invention also encompasses derivatives of the said protein, in which one of the histidines present in its sequence is modified, the said derivatives having a cytotoxic activity identical or analogous to that of the said protein without having the enzymatic activity of the latter, and being modified by fixation to the said histidine of an alkyl group of the formula R-CH$_2$-X, in which X is a halogen atom, preferably a bromine atom, and R is an aliphatic or aromatic group containing from 1 to 20 carbon atoms.

The alkylating agent is preferably fixed to the histidine in position 47 of the protein according to the invention, and may be advantageously bromophenacyl bromide.

The present invention further relates to conjugates, wherein the said protein, fragments and/or derivatives are coupled to a substance for selective transport to an appropriate target, especially to a tumoral cell, which said transport substance is selected from the group comprising hormones, polyclonal immunoglobulins and monoclonal immunoglobulins.

The present invention further relates to a method of obtaining the phospholipase A2 (PLA2) according to the invention, wherein the said protein is extracted from the venom of a snake of the family Elapidae, especially of a Naja snake and more particularly *Naja nigricollis* or *Naja mossambica pallida*, by ion exchange chromatography followed by elution with an alkaline salt of a weak organic acid, especially ammonium acetate, the eluted fractions with enzymatic activity being subjected to ion exchange chromatography a second time and the protein isolated in this way then being subjected to high performance liquid chromatography for purification.

The present invention further relates to a method of obtaining derivatives according to the invention, wherein, in a first step, the phospholipase A2 (PLA2) is isolated by the method described above, and in a second step, the said phospholipase A2 is brought into contact with an alkylating agent of the type R-CH$_2$-X, in which X is a halogen atom, and R is an aliphatic or aromatic group containing from 1 to 20 carbon atoms, in order to modify the phospholipase at one of the histidines present in its sequence by fixation of the alkylating agent to the said histidine.

The alkylating agent is preferably fixed to the histidine in position 47 of the said PLA2, and may be advantageously bromophenacyl bromide.

In a modified embodiment, the derivatives of the phospholipase A2 are obtained by a genetic engineering method wherein the cDNA coding for the said protein is modified genetically at the fragment 44-50 defined as above.

The present invention further relates to a method of obtaining fragments according to the invention, wherein the said fragments are obtained by proteolytic scission, especially tryptic and/or chymotryptic scission.

The present invention further relates to a therapeutic composition which comprises an active amount of at least one derivative and/or fragment of the phospholipase A2, which may or may not be coupled to a transport molecule, as the active principle, especially for the treatment of cancers, the said derivative and/or fragment optionally being associated with any vehicle suitable for its administration.

The present invention further relates to an agent for detecting tumoral cells, which essentially consists of a derivative and/or fragment of the phospholipase A2, obtained according to the present invention.

The present invention further relates to a ready-to-use kit for detecting tumoral cells, which comprises:

an appropriate amount, optionally subdivided into unit doses, of a derivative or fragment according to the invention, and optionally an appropriate amount of buffers, diluents and reagents necessary for carrying out the said detection.

In an advantageous embodiment of the said kit, the derivative is pBp-PLA2 obtained by fixation of bromophenacyl bromide to the histidine in position 47 of the phospholipase A2 according to the invention.

In addition to the foregoing variants, the invention also includes other variants which will become apparent from the following description, which comprises an Example of the preparation of a phospholipase A2 derivative and also an account of experiments performed in order to demonstrate the specific cytotoxic activity of the derivatives and/or fragments according to the invention towards tumoral cells and the good tolerance of the said derivatives and/or fragments by comparison with the phospholipase A2 from the venom of *Naja nigricollis*.

It must be clearly understood, however, that this Example and this account of experiments are given solely in order to illustrate the subject of the invention without in any way implying a limitation.

DESCRIPTION OF PREFERRED EMBODIMENTS

Example A

Extraction and purification of the PLA2

The lyophilized venom originates from the Institut Pasteur. 3 g of venom are dissolved in 15 ml of water. After centrifugation, the solution is deposited on an ion exchange resin "Bio-rex" 70, Biorad), to which a linear gradient of ammonium acetate of between 0.14M and 1.4M is applied. Four of the 10 fractions separated in this way possess hydrolytic activity towards egg yolk lecithin, as indicated by experiments performed with a pH-stat according to a previously described method (E. A. DENNIS, J. Lipid Res., 1986, 14, 152-159). The most basic of these fractions, which is called PLA2, is again subjected to chromatography on "Bio-Rex" 70 resin in the presence of a linear gradient of between 0.60M and 0.95M. The PLA2 is finally subjected to reversed-phase high performance liquid chromatography on a wide-pore butyl column of Nucleosil 5 $\mu$m. The enzyme is eluted by a gradient of acetonitrile in a water/trifluoroacetic acid mixture.

Figure 1:
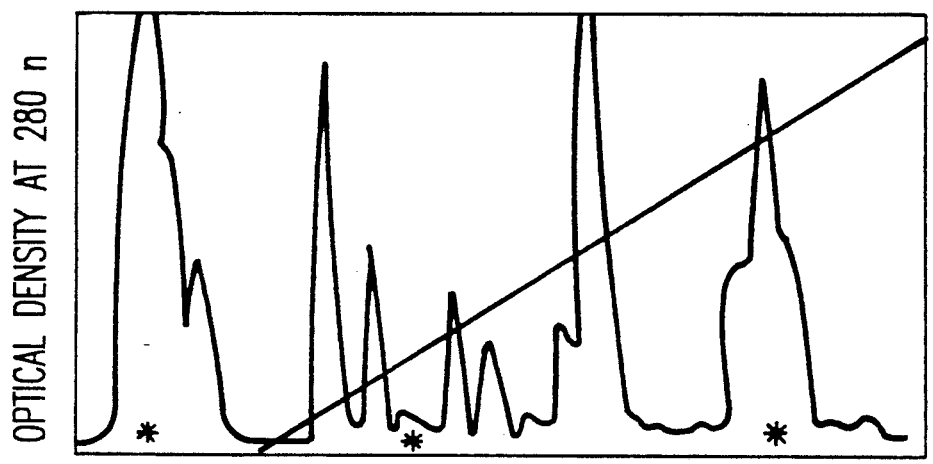

The elution profile is shown in FIG. 1, which represents the elution profile of the venom of Naja nigricollis after chromatography on "Biorex" 70 ion exchange resin. The resin had been equilibrated beforehand in a 0.14M ammonium acetate buffer of pH 7.4. The venom was then applied to the top of a column (30×1 cm). A non-retained fraction is eluted immediately. It contains a phospholipase A2, as indicated by the presence of an asterisk. After elution of this fraction, a gradient of ammonium acetate of between 0.14M and 1.4M is applied at the same pH. The most toxic phospholipase A2, also indicated by an asterisk, is eluted in the last fraction, i.e. the one furthest to the right in the Figure. It is this fraction which is again subjected to chromatography on "Biorex" resin and then to HPLC.

EXAMPLE B

Preparation of the PLA2-pBp

The PLA2 obtained according to Example A is brought into contact with parabromophenacyl bromide (pBp), which is known to interact preferentially with the histidine of the active site of phospholipases (VOLWERK et al., Biochem., 1974, 13, 1446-1454).

The experimental conditions of this treatment are as follows: 150 nmol of PLA2 are solubilized in 2 ml of sodium cacodylate buffer (0.1M) of pH 6, containing 0.1 mol/l of NaCl. An excess of pBp (5 molar) in 50 $\mu$l of acetone is added to this solution. After 5 hours of continuous stirring in the dark at 30° C., the pH of the reaction mixture is brought down to 3 by the addition of glacial acetic acid. The sample is lyophilized and then subjected to high performance liquid chromatography (wide-pore butyl column). The product is eluted in a gradient of increasing hydrophobicity (acetonitrile).

PHARMACOLOGICAL TESTS

Example 1

Comparison of the sequence of the PLA2 and its pBp derivative

Amino acid sequence of the PLA2

The complete amino acid sequence of the basic phospholipase from the venom of *Naja nigricollis* is determined on the basis of the peptides obtained by cleavage with cyanogen bromide and by proteolysis with *A. Lyticus lysylendopeptidase* and *S. aureus* V8 protease.

The protein comprises 118 amino acids and has 14½-cystine residues.

Fractionation of the phospholipase treated with cyanogen bromide and carboxymethylated produces 3 peptides of 8, 49 and 61 amino acids respectively.

Other sequences can be obtained by other fragmentations. Overlapping of these different sequences made it possible to establish the sequence of the PLA2.

pBp Derivative

The derivative pBp-PLA2 has lost one histidine per molecule and its molar extinction coefficient at 276.5 nm is 45,500.

EXAMPLE 2

Comparative Toxicity of the PLA2 and its Derivatives

The PLA2 and its derivatives were separately injected intravenously into mice (18-20 g, Balb c, female). The PLA2 and its derivatives are dissolved in 0.3 ml of physiological saline. A dose of 10 $\mu$g of unmodified PLA2 is lethal to each mouse. On the other hand, a dose of 2.3 mg of PLA2-pBp is non-lethal to each mouse.

TABLE I

| PROTEINS | $LD_{50}$ |
|---|---|
| Basic native PLA2 | $5.7 \pm 0.2 \cdot 10^{-10}$ mol |
| | $(7.7 \pm 0.3 \ \mu g)$ |
| CNBr - PLA2 | $>1.63 \cdot 10^{-7}$ mol |
| pBp - PLA2 | $>1.60 \cdot 10^{-7}$ mol |

Table I shows the $LD_{50}$ values of the PLA2, the derivative pBp-PLA2 and the derivative treated with CNBr. The toxicity was measured by injecting the doses indicated, solubilized in 0.3 ml of physiological saline, into the caudal vein of the Balb c mice (20±1 g). The survival rate is observed 24 hours after injection and then, if necessary, every day for at least one week. The sign > means that, at the dose indicated, the mice which have had an injection have not died.

The PLA2 is characterized by a substantial lethal activity. By contrast, the two derivatives are non-toxic.

EXAMPLE 3

Measurement of the Cytotoxic Activity of the PLA2 and its pBp Derivative

The cytotoxic activities of the phospholipase PLA2 and its pBp derivative are measured in the following manner: a suspension of cells of a defined homogeneous strain, containing $3.5.10^6$ cells per ml in a PBS-DULBECCO medium free of calcium and magnesium, receives variable amounts of phospholipase or its derivative. Incubation is carried out for one hour at 37° C. The dye trypan blue is added to the medium. Only the cytolyzed cells fix this dye. Measurement of the number of cytolyzed cells makes it possible to assess the cytotoxic activity of the compound studied. This cytotoxic activity is quantified by the concentration of compound which kills 50% of the cells studied ($AC_{50}$), with the background subtracted. Table II below shows the cytotoxic concentrations ($AC_{50}$) of the PLA2 and its pBp derivative in respect of eight cell lines, five of which are tumoral and three healthy.

TABLE II

| CELL STRAINS | PLA2 $AC_{50}$ (M) | PLA2 - pBp $AC_{50}$ (M) |
|---|---|---|
| Transformed | | |
| MCF7 (Ho) | $1.5 \cdot 10^{-6}$ | $3 \cdot 10^{-5}$ |
| HLGO (Ho) | $3 \cdot 10^{-6}$ | $5.5 \cdot 10^{-5}$ |
| SK-N-SH (Ho) | $5 \cdot 10^{-6}$ | $4 \cdot 10^{-6}$ |
| BW (Mu) | $3 \cdot 10^{-6}$ | $>8 \cdot 10^{-5}$ |
| C13T (Mu) | $3 \cdot 10^{-6}$ | $3 \cdot 10^{-5}$ |
| Normal | | |
| Murine peritoneal cells | $10^{-5}$ | $>8 \cdot 10^{-5}$ |
| Murine splenic cells | $10^{-6}$ | $>4 \cdot 10^{-5}$ |
| Murine T lymphocytes | $5 \cdot 10^{-6}$ | $>8 \cdot 10^{-5}$ |

This Table indicates the concentrations of phospholipase A2 (PLA2) or modified phospholipase A2 (pBp-PLA2) which it is necessary to use in order to kill transformed or normal cells. The expression >x (in which x represents a concentration expressed in mol/l) indicates that the cells in question do not die in the presence of the said concentration of PLA2 or its derivative.

It is seen that the natural PLA2 is cytotoxic to all the cell strains studied, whether they be healthy or tumoral. On the other hand, the derivative PLA2-pBp is characterized by a selective cytotoxicity to the tumoral cells. Four of the five transformed strains are destroyed by this substance, whereas the three healthy cell lines are not affected.

Figure 2:
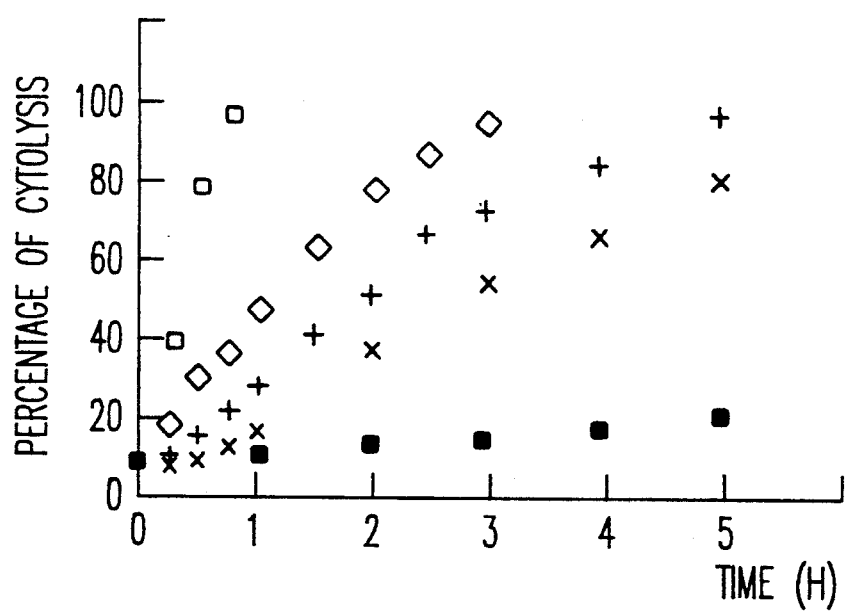

FIG. 2 shows the kinetics of cytolysis of FL cells in the presence of different concentrations of PLA2 from the venom of Naja nigricollis; the time in hours is plotted on the abscissa and the percentage cytolysis is plotted on the ordinate:

□ corresponds to 2 μmol/l of PLA2
  corresponds to 1 μmol/l of PLA2
+ corresponds to 0.5 μmol/l of PLA2
× corresponds to 0.25 μmol/l of PLA2
  corresponds to 0 μmol/l of PLA2

Membrane lysis of the cells is disclosed by a trypan blue penetration test.

This Figure shows that the basic PLA2 is highly cytotoxic and that the cytotoxic effect of the PLA2 depends on both the incubation time and the PLA2 concentration.

EXAMPLE 4

Measurement of the Enzymatic Activity of the PLA2 and its Derivatives

The enzymatic activity corresponds to the amount of enzyme which hydrolyzes 1 μmol per minute of phosphatidylcholine at a concentration of $5.5.10^{-2}$M, in the presence of 0.11M Triton X100, at 40° C. and pH 8. The values of $V_{max}$ are determined under the same conditions using $10^{-8}$ mol/l of PLA2.

Table III below shows that the basic PLA2 has lipolytic activity on egg yolk lecithin. The catalytic activity is appreciably greater in the presence of $Ca^{++}$ than in the presence of $Sr^{++}$ and is not detected in the presence of EDTA, even at PLA2 concentrations of $10^{-6}$M.

TABLE III

| | Enzymatic activity (pmol of PLA2) | Km (mM) | $V_{max}$ (μM NaOH/min.) |
|---|---|---|---|
| PLA2 ($Ca^{++}$) | 20 ± 2 | 7.53 ± 0.20 | 500 ± 14 |
| PLA2 ($Sr^{++}$) | 59 ± 3 | 7.51 ± 0.20 | 170 ± 10 |
| PLA2 (EDTA) | none | | |
| CNBr - PLA2 ($Ca^{++}$) | 294 ± 11 | 16.30 ± 0.25 | 35 ± 5 |
| pBp - PLA2 ($Ca^{++}$) | none | | |

The derivative pBp-PLA2 according to the invention has no detectable enzymatic activity; the derivative CNBr-PLA2 has a weak but significant catalytic activity.

Figure 3:
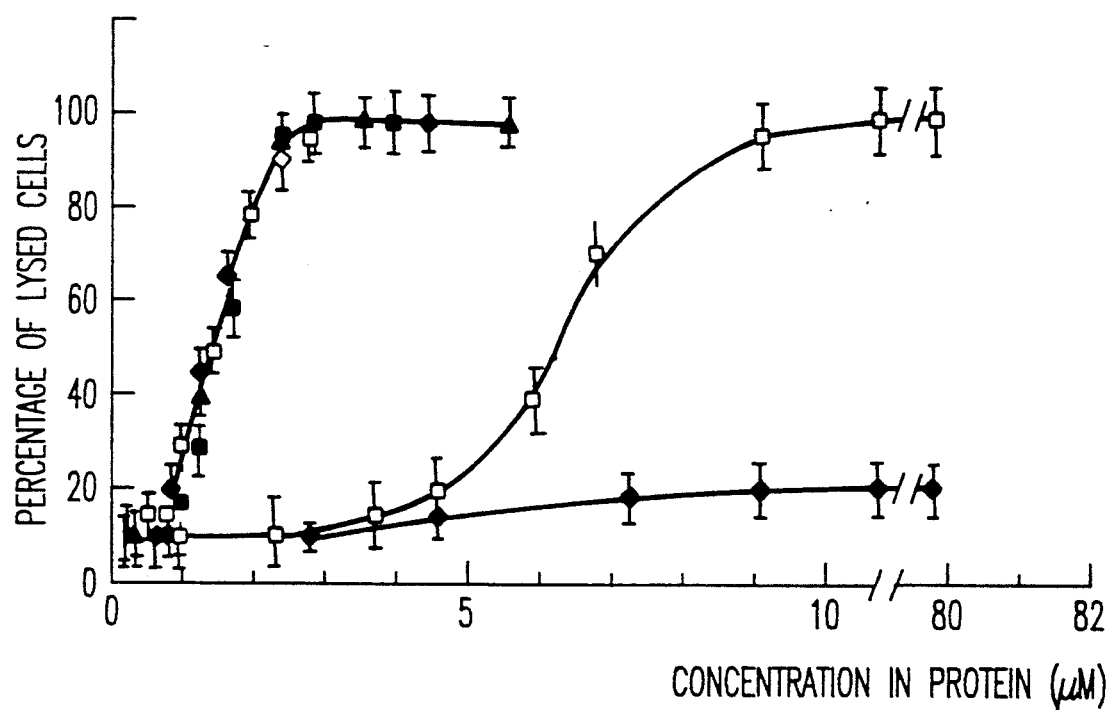

FIG. 3 shows the lysis of FL cells after incubation for 60 min. in the presence of different concentrations of PLA2 (with 6 mM EDTA, 2 mM $Sr^{++}$, 2 mM $Ca^{++}$) and of derivatives chemically treated with cyanogen bromide and parabromophenacyl bromide (□). These experiments were performed at 37° C. except in the case of (2 mM $Ca^{++}$ at 4° C.). The other conditions are those of FIG. 2.

The protein concentration in μM is plotted on the abscissa and the percentage of cells lyzed is plotted on the ordinate.

As shown in this Figure, the dose-response curves obtained with the PLA2 are identical in the presence or absence of calcium, in the presence of absence of strontium and in the presence or absence of EDTA.

It was proved that the presence of high concentrations of divalent cations or EDTA does not modify the stability of the cells during the incubation period.

Membrane lysis of the cells is carried out on FL cells at 37° C. or at 4° C. for 60 min., but no significant difference was observed for the curves at 4° C.

Two PLA2 derivatives were also tested; these were the pBp-PLA2 according to the invention, obtained after treatment with bromophenacyl bromide, and the derivative resulting from the cleavage of the PLA2 with cyanogen bromide in an acid medium.

FIG. 3 shows that the derivative pBp-PLA2 has cytotoxic activity towards the FL cells, whereas the derivative treated with CNBr has no cytotoxic activity.

As is apparent from the foregoing description, the invention is in no way limited to those embodiments and methods of application which have now been explicitly described; on the contrary, it encompasses all the variants thereof which may occur to those skilled in the art, without deviating from the framework or the scope of the present invention.

What is claimed is:

1. A derivative of a substantially pure protein of the PLA2 type of 118 amino acids, said protein having a molecular weight of approximately 13,325 daltons, having an isoelectric point of about 8.6, and having the following sequence of amino acids of formula (I) below:

Asn$^1$—Leu—Tyr—Gln—Phe—Lys—Asn—Met— (I)

Ile—His$^{10}$—Cys—Thr—Val—Pro—Ser—Arg—Pro—

Val—Val—His$^{20}$—Phe—Ala—Asp—Tyr—Gly—

Cys—Tyr—Cys—Gly—Arg$^{30}$—Gly—Gly—Lys—Gly—

Thr—Pro—Ile—Asp—Asp—Leu$^{40}$—Asp—Arg—Cys—Cys—

Gln—Val—His—Asp—Asn—Cys$^{50}$—

Tyr—Glu—Lys—Ala—Gly—Lys—Met—Gly—Cys—Trp$^{60}$—

Pro—Tyr—Phe—Thr—Leu—Tyr—Lys—

Tyr—Lys—Cys$^{70}$—Ser—Lys—Gly—Thr—Leu—Thr—

Cys—Asn—Gly—Arg$^{80}$—Asn—Gly—Lys—

Cys—Ala—Ala—Ala—Val—Cys—Asn$^{90}$—Cys—Asp—Leu—

Val—Ala—Ala—Asn—Cys—Phe—

Ala$^{100}$—Gly—Ala—Pro—Tyr—Ile—Asn—Ala—Asn—Tyr—

Asn$^{110}$—Ile—Asp—Phe—Lys—Lys—

Arg—Cys—Gln$^{118}$—OH in which the histidine present in position 47 in the sequence of the protein is modified, said derivative having a cytotoxic activity specifically directed against tumoral cells without having the enzymatic activity of the protein of formula I and being modified by a selective alkylation of the histidine by an alkyl group obtained from a compound of the formula:

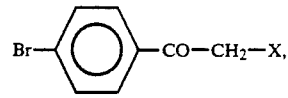

in which X is a halogen atom.

2. A method of preparing a compound having cytotoxic activity, which comprises reacting a cytotoxic agent with a compound of the formula R-CH$_2$-X, wherein R is an aliphatic or aromatic group of from 1 to 20 carbon atoms and X is a halogen atom, and said cytotoxic agent comprising a substantially pure protein of the PLA2 type of 118 amino acids, said protein having a molecular weight of approximately 13,325 daltons, and having an isoelectric point of about 8.6, and having the following sequence of amino acids of formula (I) below:

Asn$^1$—Leu—Tyr—Gln—Phe—Lys—Asn—Met—Ile—His$^{10}$— (I)
Cys—Thr—Val—Pro—Ser—Arg—Pro—Val—Val—His$^{20}$—
Phe—Ala—Asp—Tyr—Gly—Cys—Tyr—Cys—Gly—Arg$^{30}$—
Gly—Gly—Lys—Gly—Thr—Pro—Ile—Asp—Asp—Leu$^{40}$—
Asp—Arg—Cys—Cys—Gln—Val—His—Asp—Asn—Cys$^{50}$—
Tyr—Glu—Lys—Ala—Gly—Lys—Met—Gly—Cys—
Trp$^{60}$—Pro—Tyr—Phe—Thr—Leu—Tyr—Lys—Tyr—Lys—
Cys$^{70}$—Ser—Lys—Gly—Thr—Leu—Thr—Cys—Asn—Gly—
Arg$^{80}$—Asn—Gly—Lys—Cys—Ala—Ala—Ala—Val—Cys—
Asn$^{90}$—Cys—Asp—Leu—Val—Ala—Ala—Asn—Cys—
Phe—Ala$^{100}$—Gly—Ala—Pro—Tyr—Ile—Asn—Ala—Asn—
Tyr—Asn$^{110}$—Ile—Asp—Phe—Lys—Lys—Arg—Cys—
Gln$^{118}$—OH whereby the histidine residue at position 47 of said cytotoxic agent is selectively alkylated.

* * * * *